US008729229B2

(12) United States Patent
Ray et al.

(10) Patent No.: US 8,729,229 B2
(45) Date of Patent: May 20, 2014

(54) PROCESSES FOR PREPARING A POLYPEPTIDE

(75) Inventors: Anup Kumar Ray, Staten Island, NY (US); Hiren Kumar V. Patel, Fords, NJ (US); Johannes Ludescher, Breitenbach (AU); Mariappan Anbazhagan, Monmouth Junction, NJ (US); Mahendra R. Patel, Milltown, NJ (US); Ingolf Macher, Woergl (AU)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 12/726,571

(22) Filed: Mar. 18, 2010

(65) Prior Publication Data

US 2010/0234272 A1    Sep. 16, 2010

Related U.S. Application Data

(60) Division of application No. 11/904,422, filed on Sep. 27, 2007, which is a continuation of application No. 11/262,122, filed on Oct. 28, 2005, now abandoned.

(60) Provisional application No. 60/723,901, filed on Oct. 5, 2005, provisional application No. 60/651,535, filed on Feb. 9, 2005, provisional application No. 60/651,372, filed on Feb. 9, 2005, provisional application No. 60/623,346, filed on Oct. 29, 2004.

(51) Int. Cl.
*A61K 38/00* (2006.01)
*C07K 1/00* (2006.01)
*C07K 2/00* (2006.01)

(52) U.S. Cl.
USPC ............ 530/333; 514/1.1; 530/300; 530/335; 530/336; 530/337; 530/344; 530/350

(58) Field of Classification Search
None
See application file for complete search history.

(56) References Cited

U.S. PATENT DOCUMENTS

| | | | |
|---|---|---|---|
| 2,657,972 A | | 11/1953 | Woodward |
| 3,704,282 A | | 11/1972 | Spector |
| 3,849,550 A | | 11/1974 | Teitelbaum et al. |
| 4,594,409 A | | 6/1986 | Hayashi et al. |
| 5,800,808 A | | 9/1998 | Konfino et al. |
| 5,981,589 A | * | 11/1999 | Konfino et al. ............... 514/561 |
| 6,048,898 A | | 4/2000 | Konfino et al. |
| 6,054,430 A | | 4/2000 | Konfino et al. |
| 6,214,791 B1 | | 4/2001 | Arnon et al. |
| 6,342,476 B1 | | 1/2002 | Konfino et al. |
| 6,362,161 B1 | | 3/2002 | Konfino et al. |
| 6,514,938 B1 | | 2/2003 | Gad et al. |
| 6,620,847 B2 | | 9/2003 | Konfino et al. |
| 6,936,539 B2 | | 8/2005 | Yin et al. |
| 7,049,399 B2 | * | 5/2006 | Bejan et al. .................... 530/333 |
| 7,074,580 B2 | | 7/2006 | Gad et al. |
| 7,163,802 B2 | | 1/2007 | Gad et al. |
| 2004/0091956 A1 | * | 5/2004 | Bejan et al. .................. 435/68.1 |
| 2005/0159336 A1 | | 7/2005 | Eisenbach-Schwartz et al. |

FOREIGN PATENT DOCUMENTS

| | | |
|---|---|---|
| EP | 0378246 | 7/1990 |
| EP | 0383620 | 8/1990 |
| EP | 0417588 | 3/1991 |
| RU | 1690368 | 8/1995 |
| RU | 1469826 | 11/1995 |
| WO | 95/31990 | 11/1995 |
| WO | 2004/043995 | 5/2004 |

OTHER PUBLICATIONS

Keith et al., The Effect of COP-1, a Synthetic Polypeptide, on Chronic Relapsing Experimental Allergic Encephalomyelitis in Guinea Pigs, Journal of Neurol. Science, 1979, vol. 42 pp. 267-274.
Borenstein et al., Clinical Experience With COP-1 in Multiple Sclerosis, Neurology, 1988, vol. 38 (No. 7 suppl 2), pp. 66-69.
Borenstein et al., Rationale for Immunomodulating Therapies of Multiple Sclerosis, Neurology, 1988, vol. 38 (No. 7 suppl 2), pp. 80-81.
Borenstein et al., A Pilot Trial of COP-1 in Exacerbating -Remitting Multiple Sclerosis, New England Journal of Medicine, 1987, vol. 317, (No. 7), pp. 408-414.
Borenstein, Hopeful Prospects in Multiple Sclerosis, Hospital Practice, Clinical Experience, May 1992, vol. 27 (No. 5), pp. 135-138, 141-142, 145-158.
Borenstein et al., A Placebo-Controlled, Double-Blind, Randomized, Two-Center, Pilot Trial of COP-1 in Chronic Progressive Multiple Sclerosis, Neurology, 1991, vol. 41, (No. 4), pp. 533-539.
Weinshenker et al., Natural History and Treatment of Multiple Sclerosis, Current Opinion in Neurology and Neurosurgery, 1992, vol. 5, pp. 203-211.
Brosnan et al., Copolymer 1: Effect on Normal Human Lymphocytes, Ann. New York Academy of Science, 1984, vol. 436, pp. 498-499.
Brosnan et al., Immunogenic Potentials of Copolymer 1 in Normal Lymphocytes, Neurology, 1985, vol. 35, pp. 1754-1759.
Brosnan et al., The Response of Normal Human Lymphocytes to Copolymer 1, Journal of Neuropath. Exp. Neurology, 1983, vol. 42, pp. 356 (abstract).
Webb et al., Further Studies on the Suppression of Experimental Allergic Encephalomyelitis by Synthetic Copolymer, Israel Journal of Medical Science, 1972, vol. 8, pp. 656-657.
Webb et al., In Vivo and In Vitro Immunological Cross-Reactions Between Basic Encephalitogen and Synthetic Basic Polypeptides Capable of Suppressing Experimental Allergic Encephalomyelitis, European Journal of Immunology, 1973, vol. 3, pp. 279-286.
Webb et al., Molecular Requirements Involved in Suppression of EAE by Synthetic Basic Copolymers of Amino Acids, Immunochemistry, 1976, vol. 13, pp. 333-337.
Webb et al., Suppression of Experimental Allergic Encephalomyelitis in Rhesus Monkeys by a Synthetic Basic Copolymer, Israel Journal of Medical Science, 1975, vol. 11, pp. 1388 (abstract).

(Continued)

*Primary Examiner* — Maury Audet
(74) *Attorney, Agent, or Firm* — Luedeka Neely Group, P.C.; J. David Gonce

(57) ABSTRACT

The present invention relates to processes for preparing a polypeptide or pharmaceutically acceptable salt thereof comprising L-tyrosine, L-alanine, L-glutamate, and L-lysine. The polypeptide or pharmaceutically acceptable salt thereof is preferably glatiramer acetate.

20 Claims, No Drawings

(56) References Cited

OTHER PUBLICATIONS

Clinical Trial Protocol No. 9001; First Patient Enrolled Oct. 23, 1991.
Clinical Trial Protocol No. 9002; First Patient Enrolled in Jun. 17, 1993.
Francis, The Current Therapy of Multiple Sclerosis, Journal of Clinical Pharmacy and Therapeutics, 1993, vol. 18, pp. 77-84.
Teitelbaum et al., Blocking of Sensitization to Encephalitogenic Basic Protein in Vitro by Synthetic Basic Copolymer (COP-1), Cell Biology and Immunology of Leukocyte Function, Academic Press, 1979, pp. 681-685.
Teitelbaum et al., Cross-Reactions and Specificities of Monoclonal Antibodies Against Myelin Basic Protein and Against the Synthetic Copolymer 1, Proc. Natl. Acad. Sci., 1991, vol. 88, pp. 9528-9532.
Teitelbaum et al., Dose-Response Studies in Experimental Allergic Encephalomyelitis Suppression by COP-1, Israel Journal of Medical Science, 1974, vol. 10, pp. 1172-1173.
Teitelbaum et al., Immunological Parameters in a Multicenter Clinical Trial of COP 1 in Multiple Sclerosis: A 2 Year Follow Up, Neurology, 1994, vol. 44 (Suppl 2), A358.
Teitelbaum et al., Monoclonal Antibodies to Myelin Basic Protein Cross React With a Synthetic EAE Suppressive Copolymer, COP 1, Proc. 7th European Immunology Meeting, Jerusalem, 1985 (Abstract).
Teitelbaum et al., Protection Against Experimental Allergic Encephalomyelitis, Nature, 1972, vol. 240, pp. 564-566.
Teitelbaum et al., Suppression of Experimental Allergic Encephalomyelitis by a Synthetic Polypeptide, European Journal of Immunology, 1971, vol. 1, pp. 242-248.
Teitelbaum et al., Suppression by Several Synthetic Polypeptides of Experimental Allergic Encephalomyelitis Induced in Guinea Pigs and Rabbits With Bovine and Human Basic Encephalitogen, European Journal of Immunology, 1973, vol. 3, pp. 273-279.
Teitelbaum et al., Suppression of Experimental Allergic Encephalomyelitis in Rhesus Monkeys by a Synthetic Basic Copolymer, Clin. Immunol. Immunopath, 1974, vol. 3, pp. 256-262.
Teitelbaum et al., Suppression of Experimental Allergic Encephalomyelitis in Baboons by COP-1, Israel J. Med. Sci., 1977, vol. 13, pp. 1038 (abstract).
Teitelbaum et al., Synthetic Copolymer 1 Inhibits Human T-Cell Lines Specific for Myelin Basic Protein, Proc. Natl. Acad., Sci., 1992, vol. 89, pp. 137-141.
Teitelbaum, Suppression of Experimental Allergic Encephalomyelitis with a Synthetic Copolymer-relevance to Multiple Sclerosis, Humoral Immunity in Neurological Diseases, 1979, pp. 609-613.
Teitelbaum et al., article entitled "Experiment in Treating Multiple Sclerosis with Copolymre 1 (COP)", Harefuah, Journal of the Israel Medical Association, vol. CXVI, No. 9, May 1, 1989, Jerusalem (full translation).
Grgacic et al., Cell-mediate Immune Response to Copolymer 1 in Multiple Sclerosis Measured by the Macrophage Procoagulant Activity Assay, Int. Immunol, 1990, vol. 2, pp. 714-718.
Gurevich, Study of the MHC-competition between BP and Cop 1 using human cytotoxic T-cell clones, Israel J. Med. Sci, 1993 (Abstract).
Kott et al., COP-1 Increases Suppressor Cells Number In Multiple Sclerosis, Israel Neurological Association, 1994, p. 17.
Alvord et al., Myelin Basic Protein Treatment of Experimental Allergic Encephalomyelitis in Monkeys, Ann. Neurol, 1979, vol. 6, pp. 469-473.
Winer, COP-1 Therapy for Multiple Sclerosis, New England Journal of Medicine, 1987, vol. 317, pp. 442-444.
Burns et al., Failure of Copolymer 1 to Inhibit the Human T-cell Response to Myelin Basic Protein, Neurology, 1991, vol. 41, pp. 1317-1319.
Burns et al., Human Cellular Immune Response In Vitro to Copolymer 1 and Myelin Basic Protein (MBP), Neurology, 1985, vol. 35 (suppl 1), pp. 170 (abstract).
Burns et al., Human Cellular Immune Response to Copolymer 1 and Myelin Basic Protein, Neurology, 1986, vol. 36, pp. 92-94.

McDermott et al., Antigen-induced Suppression of Experimental Allergic Neuritis in the Guinea Pig, J. Neurol. Sci., 1980, vol. 46, pp. 137-143.
Johnson et al., Copolymer 1 Reduces Relapse Rate and Improves Disability in Relapsing-Remitting Multiple Sclerosis, Neurology, Jul. 1995, vol. 45 (No. 7), pp. 1268-1276.
Carter et al., Newer Drug Therapies for Multiple Sclerosis, Drug Therapy, Mar. 1990, pp. 31-43.
Johnson, Clinical Studies in Copolymer 1 Therapy for Exacerbating-remitting Multiple Sclerosis, Comm. presented at the Congress for Advances in the Understanding and Treatment of Multiple Sclerosis, Boston (USA), Oct. 28-29, 1992.
Johnson, Experimental Therapy of Relapsing-Remitting Multiple Sclerosis With Copolymer-1, American Neurological Association, 1994, vol. 36, pp. 115-117.
Korczyn et al., Safety Profile of Copolymer 1: Analysis of Cumulative Experience in the United States and Israel, Journal of Neurology, Apr. 1996; vol. 243 (4 Suppl 1) pp. S23-S26.
Durelli, Immunotherapeutics of Multiple Sclerosis, 1994, pp. 467-475.
Jacobs, Advances in specific therapy for multiple sclerosis, Neurology, 1994, 7, pp. 250-254.
Myers et al., The Peculiar Difficulties of Therapeutic Trials for Multiple Sclerosis, Neurologic Clinics, Feb. 1990, vol. 8, pp. 119-141.
Salvetti et al., Myelin Basic Protein T Cell Epitopes in Patients with Multiple Sclerosis, 1991, 72 (Abstract).
Bornstein et al., Clinical Trials of a Synthetic Polypeptide (Copolymer 1) for the Treatment of Multiple Sclerosis, R. E. Gonsett et al., eds. Immunological and clinical aspects of multiple sclerosis, 1984, pp. 144-150.
Bornstein et al., Clinical Trials of COP-1 in Multiple Sclerosis, Handbook of Multiple Sclerosis, S. D. Cook Marcel Rekker ed., 1990, pp. 469-480.
Bornstein et al., Clinical Trials of Copolymer 1 in Multiple Sclerosis, Ann. N.Y. Acad. Sci. (USA), 1984, pp. 366-372.
Bornstein et al., Multiple Sclerosis: Clinical Trials of a Synthetic Polypeptide, Copolymer 1, Neurology, 1985, 35, (suppl 1), p. 103 (abstract).
Bornstein et al., Pilot Trial of COP-1 in Chronic Progressive Multiple Sclerosis: Preliminary Report, Elsevier Science Publisher, 1989, pp. 225-232.
Bornstein et al., Multiple Sclerosis: Trial of a Synthetic Polypeptide, Ann. Neurol., 1982, vol. 11, pp. 317-319.
Bornstein et al., Treatment of Multiple Sclerosis with a Synthetic Polypeptide: Preliminary results, Trans. Am. Neurol. Assoc., 1980, vol. 105, pp. 348-350.
Bornstein et al., Treatment of Multiple Sclerosis: Trial design, results and future Perspectives, Rudick R.K. & Goodkin D.E., eds. Springer Verlag, London, New York, 1992, pp. 173-198.
Bornstein, COP-1 may be Beneficial for Patients with Exacerbating-remitting Form of Multiple Sclerosis, Adv. Ther. (USA), 1987, vol. 4, p. 206 (Abstract).
Bodanszky, Principles of Peptide Synthesis, Springer-Verlag, Berlin, Heidelberg, New York, Tokyo, 1984, 118-229.
Fridkis-Hareli et al., Copolymer 1 Displaces MBP, PLP and MOG, but can not be displaced by these antigens from the MHC Class II binding Site, 1994.
Fridkis-Hareli et al., Specific and Promiscuous Binding of Synthetic Copolymer-1 to Class II Major Histocompatibility Complex Molecules on Living Antigen Presenting Cells, Israeli Biochemistry Society, Mar. 1994, pp. 21-22 (Abstract).
Fridkis-Hareli et al., Synthetic Copolymer-1 and Myelin Basic Protein do not Undergo Processing Prior to the Binding to Class II Major Histocompatibility Complex Molecules on Antigen Presenting Cells, The Israeli Immunol. Soc., May 3-4, 1994, (Abstract).
Fridkis-Hareli et al., Synthetic Copolymer-1 Inhibits the Binding of MBP, PLP and MOG Peptides to Class II Major Histocompatibility Complex Molecules on Antigen Presenting Cells, Neurochem Meeting, Aug. 14-19, 1994.
Sela et al., Experimental Allergic Encephalomyelitis in Menarini Series on Immunopathology, vol. 1, First Symposium of Organ Specific Autoimmunity, Cremona, Italy, Jun. 1977, Miescher P.A. ed., pp. 9-21, Schwabe Co., Basel, (1978).

(56) References Cited

OTHER PUBLICATIONS

Sela, Polymeric Drugs as Immunomodulatory Vaccines Against Multiple Sclerosis, Makromol. Chem. Macromol. Symp., 1993, vol. 70/71, pp. 147-155.

Wender, Copolymer 1 (COP-1) in the Treatment of Multiple Sclerosis (letter) Neur. Neurochir. Pol. (Poland), 1990, 24, pp. 113.

Fridkis-Hareli et al., Direct binding of myelin basic protein and synthetic copolymer 1 to class II major histocompatibility complex molecules on living antigen-presenting cells-specificity and promiscuity, Proc. Natl. Acad. Sci., USA, May 1994, 91, pp. 4872-4876.

Fridkis-Hareli et al., Synthetic Copolymer 1 and Myelin Basic Protein Do Not Require Processing Prior to Binding To Class II Major Histocompatibility Complex Molecules on Living Antigen Presenting Cells, J. Neurochem, vol. 63, Suppl. 1, pp. 561, 1994.

Abramsky et al., Effect of a Synthetic Polypeptide (COP-1) on Patients with Multiple Sclerosis and with Acute Disseminated Encephalomyelitis, J. Neurol. Sci., 1977, vol. 31, pp. 433-438.

Cotton, Options for Multiple Sclerosis Therapy, JAMA Medical News & Perspectives, 1994, 272, No. 18.

Arnon et al., Desensitization of Experimental Allergic Encephalomyelitis with Synthetic Peptide Analogues, The Suppression of Experimental Allergic Encephalomyelitis and Multiple Sclerosis, Academic Press, New York, 1980 pp. 105-107.

Arnon et al., Immunospecific Drug Design-Prospects for Treatment of Autoimmune Diseases, Therapeutic Immunol., 1994, 1, pp. 65-70.

Arnon et al., On the Existence of Suppressor Cells, Int. Arch. Allergy Immunol., 1993, vol. 100, pp. 2-7.

Arnon et al., Suppression of Demyelinating Diseases by Synthetic Copolymers, from: A multidisciplinary approach to myelin disease G. Serlupi Crescenzi, ed. Plenum Publishing Corporation, 1988, pp. 243-250.

Arnon et al., Suppression of EAE in Baboons by a Synthetic Polymer of Amino Acids, Neurology, 1978, vol. 28, 336 (abstract).

Arnon et al., Suppression of Experimental Allergic Encephalomyelitis by a Synthetic Copolymer Immunological Cross Reactive with Basic Encephalitogen, Israel J. Med. Sci., 1972 vol. 8, pp. 1759-1760.

Arnon, A Synthetic Copolymer of Amino Acids in a Clinical Trail for MS Therapy, Progress in Multiple Sclerosis Research, Bauer, Ritter, eds. Springer Verlag N.Y., 1980 pp. 416-418.

Arnon, Experimental Allergic Encephalomyelitis-Susceptibility and Suppression, Immunological Rev., 1981, vol. 55, pp. 5-30.

Milo et al., Additive Effect of Copolymer-1 and Interferon-B on the Immune Response to Myelin Basic Protein, Assaf Harofeth Medical Center, Sackler School of Medicine, Tel-Aviv University, Universty of Marland School of Medicine, p. 22, 1994.

Milo et al., Additive Effects of COP-1 and IFN-Beta on Immune Responses to Myelin Basic Protein, Neurologgy, 1994, vol. 44, suppl. 2 A212.

Milo et al., Copolymer-1 (COP-1) regulates class II MCH Expression and Cytokine Synthesis in the Monocyte-Macrophage Cell Line, The IBC Conference on Multiple Sclerosis, San Diego, Dec. 10, 1993 (Abstract).

Milo et al., Inhibition of Myelin Basic Protein-Specific Human T-Cell Lines by COP-1, Israel J. Med. Sci., 1992, vol. 28, p. 486 (Abstract).

Lisak et al., Effect of Treatment with Copolymer 1 (COP-1) on the in Vivo and in Vitro Manifestations of Experimental Allergic Encephalomyelitis (EAE), J. Neurol. Sci., 1983, vol. 62, pp. 281-293.

Bansil et al., Multiple Sclerosis: Pathogenesis and Treatment, Seminars in Neurology, Jun. 1994, vol. 14, No. 2, pp. 146-153.

Nightingale M.D. et al., Access to Investigational Drugs for Treatment Purposes, American Family Physician, Sep. 15, 1994, pp. 845-847.

The COP-1 Multicenter Clinical and Research Group Study, "COP-1 Multicenter Trial in Relapsing Remitting Multiple Sclerosis: 3 Year Follow Up", Abstracts of Symposia and Free Communication, Jun. 25-29, 1994, suppl 1, 241, p. 6.

Stark, Expanded Clinical Trials of Treatments for Multiple Sclerosis: Copolymer 1 Treatment Investigational New Drug Program, Ann. Neurol, 1994, 36, pp. 114-115.

Lando et al., Effect of Cyclophosphamide on Suppressor Cell Activity in Mice Unresponsive to EAE, J. Immunol, 1979, vol. 123, pp. 2156-2160 (abstract).

Lando et al., Experimental Allergic Encephalomyelitis in Mice-Suppression and Prevention with COP-1, Israel J. Med. Sci., 1979, vol. 15, pp. 868-869 (abstract).

Meiner et al., The Israel COP-1 Multicenter Clinical Trial in Exacerbating-remitting Multiple Sclerosis two-year followup, 9th Congress of the European Committee for Treatment and Research in Multiple Sclerosis, Florence (Italy), Oct.-Nov. 1993 (Abstract).

Meiner, COP-1 Multicenter Clinical Trial in Exacerbating-remitting Multiple-Sclerosis: one year follow-up, J. of Neurol., 1991, supp 1. (abstract).

Rolak, Copolymer-I Therapy for Multiple Sclerosis, Dept. of Neurology, Baylor College of Medicine, Clinical Neuropharmacology, vol. 10, No. 5, 1987, pp. 389-396.

* cited by examiner

PROCESSES FOR PREPARING A POLYPEPTIDE

CROSS-REFERENCE(S) TO RELATED APPLICATION(S)

This application is a divisional of copending application Ser. No. 11/904,422 filed Sep. 27, 2007, entitled "Processes for Preparing a Polypeptide," which is a continuation of U.S. application Ser. No. 11/262,122 filed Oct. 28, 2005, now abandoned entitled "Processes for Preparing a Polypeptide," which claims the benefit of U.S. Provisional App. Ser. No. 60/623,346 filed Oct. 29, 2004, entitled "Phase Transfer Process for Preparing Glatiramer Acetate," U.S. Provisional App. Ser. No. 60/651,372 filed Feb. 9, 2005, entitled "Process for Preparing Glatiramer Acetate Using an Amine or Ammonia," U.S. Provisional App. Ser. No. 60/651,535 filed Feb. 9, 2005, entitled "Process for Preparing Glatiramer Acetate Using an Alkali or Alkaline Earth Metal Hydroxide, a Carbonate, or a Hydrogencarbonate," and U.S. Provisional App. Ser. No. 60/723,901 filed Oct. 5, 2005, entitled "Acid Hydrolysis Process for Preparing a Polypeptide," all of the aforesaid being hereby incorporated by reference in their entireties.

FIELD OF THE INVENTION

The present invention provides processes for preparing a polypeptide or pharmaceutically acceptable salt thereof. More specifically, the invention provides processes for preparing glatiramer acetate.

BACKGROUND OF THE INVENTION

COPAXONE® is the trade name of glatiramer acetate, an FDA approved drug for the treatment of multiple sclerosis. COPAXONE® is also known as Copolymer-1. The COPAXONE® label discloses that COPAXONE® consists of the acetate salts of synthetic polypeptides, containing four naturally-occurring amino acids: L-glutamic acid, L-alanine, L-tyrosine and L-lysine with an average molar fraction of 0.141, 0.427, 0.095 and 0.338, respectively, and has a weight average molecular weight of 4.7-11.0 kilodaltons (kDa). COPAXONE® comprises a mixture of polypeptides having different molecular weights and sequences. The structural formula of COPAXONE® is:

(Glu,Ala,Lys,Tyr)$_x$·xCH$_3$COOH

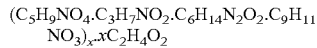

(C$_5$H$_9$NO$_4$·C$_3$H$_7$NO$_2$·C$_6$H$_{14}$N$_2$O$_2$·C$_9$H$_{11}$NO$_3$)$_x$·xC$_2$H$_4$O$_2$

COPAXONE® is a white to off-white, sterile, lyophilized powder containing 20 mg glatiramer acetate and 40 mg of mannitol. It is supplied in single use vials for subcutaneous administration after reconstitution with sterile water.

Processes for preparing Copolymer-1 or glatiramer acetate have been described in U.S. Pat. Nos. 3,849,550; 5,800,808; 5,981,589; 6,048,898; 6,054,430; 6,342,476; and 6,362,161. The process for the synthesis of glatiramer acetate is based on the polymerization of N-carboxyanhydrides of tyrosine, alanine, γ-benzyl glutamate and N$^\epsilon$-trifluoroacetyl lysine in anhydrous dioxane at room temperature using diethylamine as initiator, to form a protected polypeptide. The deblocking of the γ-benzyl groups (first deprotection) is accomplished by stirring the protected polypeptide in hydrogen bromide/acetic acid at room temperature. These conditions also facilitate the cleavage of the copolymer. The next step is the removal of the N$^\epsilon$-trifluoroacetyl groups (second deprotection) of the copolymer by treatment with 1 M piperidine. In the final steps, glatiramer acetate is obtained by purification of the copolymer through dialysis, followed by treatment with acetic acid to form the acetate salt and by another purification by dialysis against water. Thus, these prior art processes involve the polymerization of four N-carboxyanhydrides, two deprotection steps, two purification steps and one acetate salt formation step.

U.S. Pat. No. 6,620,847 describes a process for preparing Copolymer-1 which involves treating trifluoroacetyl Copolymer-1 with aqueous piperidine to form a solution of Copolymer-1 and purifying Copolymer-1.

U.S. Patent Application Publication No. 2004/0091956 describes a three-step process for preparing glatiramer acetate. The process involves polymerization of a mixture of the N-carboxyanhydrides of L-alanine, L-tyrosine, protected L-glutamate and protected L-lysine, to obtain a protected polypeptide or salt thereof; and deprotection of the protected polypeptide or salt thereof by either palladium catalytic transfer hydrogenation or palladium catalytic hydrogenation under hydrogen pressure.

SUMMARY OF THE INVENTION

The invention provides a process for preparing a polypeptide comprising L-tyrosine, L-alanine, L-glutamate and L-lysine, or a pharmaceutically acceptable salt thereof, wherein said process comprises:
(i) polymerizing a mixture of N-carboxyanhydride of L-tyrosine, N-carboxyanhydride of L-alanine; N-carboxyanhydride of protected L-glutamate; and N-carboxyanhydride of N-t-butoxycarbonyl L-lysine, in a polar aprotic solvent in the presence of an initiator, to form a protected polypeptide, wherein the protected L-glutamate is selected from the group consisting of γ-p-methoxybenzyl L-glutamate, γ-benzyl L-glutamate and mixtures thereof; and
(ii) adding an acid to the protected polypeptide formed in Step (i) to form a polypeptide or a pharmaceutically acceptable salt thereof, wherein said acid cleaves the γ-p-methoxybenzyl group from the glutamate moiety and the N-t-butoxycarbonyl group from the lysine moiety.

The invention provides a process for preparing a polypeptide comprising L-tyrosine, L-alanine, L-glutamate and L-lysine, or a pharmaceutically acceptable salt thereof, wherein said process comprises treating a protected polypeptide with an aqueous solution of an alkali or alkaline earth metal hydroxide to form a polypeptide or a pharmaceutically acceptable salt thereof.

The invention provides a process for preparing a polypeptide comprising L-tyrosine, L-alanine, L-glutamate and L-lysine, or a pharmaceutically acceptable salt thereof, wherein said process comprises:
(a)$^2$ polymerizing a mixture of N-carboxyanhydride of L-tyrosine, N-carboxyanhydride of L-alanine, N-carboxyanhydride of a protected L-glutamate and N-carboxyanhydride of a protected L-lysine, in a polar aprotic solvent in the presence of an initiator, to form a protected polypeptide;
(b)$^2$ admixing an acid with the protected polypeptide formed in Step (a)$^2$ and a solvent, to form a product; and
(c)$^2$ admixing a substance selected from the group consisting of diisopropylamine, isopropylamine, ammonia and mixtures thereof, with the product formed in Step (b)$^2$, and water or a mixture of a solvent and water, to form a deprotected polypeptide or a pharmaceutically acceptable salt thereof.

The invention provides a process for preparing a polypeptide comprising L-tyrosine, L-alanine, L-glutamate and L-lysine, or a pharmaceutically acceptable salt thereof, wherein said process comprises:
- (a)³ polymerizing a mixture of N-carboxyanhydride of L-tyrosine, N-carboxyanhydride of L-alanine, N-carboxyanhydride of a protected L-glutamate and N-carboxyanhydride of a protected L-lysine, in a polar aprotic solvent in the presence of an initiator, to form a protected polypeptide;
- (b)³ admixing an acid with the protected polypeptide formed in Step (a)³ and a solvent, to form a product; and
- (c)³ admixing a substance selected from the group consisting of an alkali or alkaline earth metal hydroxide, a carbonate, a hydrogencarbonate and mixtures thereof, with the product formed in Step (b)³, and a solvent or a mixture of a solvent and water, to form a deprotected polypeptide or a pharmaceutically acceptable salt thereof.

DESCRIPTION OF THE INVENTION

The present invention relates to processes for preparing a polypeptide or pharmaceutically acceptable salt thereof comprising L-tyrosine, L-alanine, L-glutamate and L-lysine. The polypeptide or pharmaceutically acceptable salt thereof is preferably glatiramer acetate.

I. Acid Hydrolysis Process.

In one embodiment of the invention, the process comprises:
- (i) polymerizing a mixture of N-carboxyanhydride of L-tyrosine, N-carboxyanhydride of L-alanine, N-carboxyanhydride of protected L-glutamate and N-carboxyanhydride of N-t-butoxycarbonyl L-lysine, in a polar aprotic solvent in the presence of an initiator, to form a protected polypeptide, wherein the protected L-glutamate is selected from the group consisting of γ-p-methoxybenzyl L-glutamate, γ-benzyl L-glutamate and mixtures thereof; and
- (ii) adding an acid to the protected polypeptide formed in Step (i) to form a polypeptide or a pharmaceutically acceptable salt thereof, wherein said acid cleaves the γ-p-methoxybenzyl group from the glutamate moiety and the N-t-butoxycarbonyl group from the lysine moiety.

In one embodiment of the invention, the process comprises:
- (a) polymerizing a mixture of N-carboxyanhydride of L-tyrosine, N-carboxyanhydride of L-alanine, N-carboxyanhydride of protected L-glutamate and N-carboxyanhydride of N-t-butoxycarbonyl L-lysine, in a polar aprotic solvent in the presence of an initiator, to form a protected glatiramer, wherein the protected L-glutamate is selected from the group consisting of γ-p-methoxybenzyl L-glutamate, γ-benzyl L-glutamate, and mixtures thereof;
- (b) adding an acid to the protected glatiramer formed in Step (a) to form a glatiramer, wherein said acid cleaves the γ-p-methoxybenzyl group from the glutamate moiety and the N-t-butoxycarbonyl group from the lysine moiety; and
- (c) treating the glatiramer formed in Step (b) with acetic acid to form glatiramer acetate.

In the polymerizing step of the processes of the invention, Step (i), Step (a), Step (a)¹, Step (a)¹', Step (a)², Step (a)²', Step (a)³ and Step (a)³', the mixture of N-carboxyanhydride of L-tyrosine, N-carboxyanhydride of L-alanine, N-carboxyanhydride of protected L-glutamate and N-carboxyanhydride of N-t-butoxycarbonyl L-lysine, are preferably polymerized at a temperature of from about 10° C. to about 40° C., more preferably about 20° C. to about 30° C. The polymerization reaction preferably takes place for a period of from about 2 hours to about 80 hours, more preferably from about 20 hours to about 50 hours. Most preferably, the polymerization reaction takes place for a period of about 24 hours at a temperature of about 25° C.

The polar aprotic solvent is preferably selected from tetrahydrofuran, ethyl acetate, dimethyl furan, dimethylformamide, dioxane, dimethoxyethane, 1,2-dichloroethylene, dimethylsulfoxide and dichloromethane. Most preferably, the polar aprotic solvent is 1,4-dioxane. A mixture of polar aprotic solvents may also be used.

The initiator used in Step (i), Step (a), Step (a)¹, Step (a)¹', Step (a)², Step (a)²', Step (a)³ and Step (a)³', of the processes of the invention may be any alkylamine initiator, such as a dialkyl or a trialkylamine. Each of the alkyl groups preferably has 1-6 carbon atoms. A preferred alkylamine initiator is diethylamine. Preferably, the diethylamine is present in an amount of from about 0.001 weight percent (wt. %) to about 2 wt. %, more preferably from about 0.01 wt. % to about 0.02 wt. %, based on the weight of the mixture of N-carboxyanhydride of L-tyrosine, N-carboxyanhydride of L-alanine, N-carboxyanhydride of protected L-glutamate and N-carboxyanhydride of N-t-butoxycarbonyl L-lysine.

In one embodiment of the invention, water is added to the polymerization mixture following polymerization. The addition of water results in precipitation of the protected polypeptide. The water is preferably removed from the mixture containing water and protected polypeptide by vacuum filtration and the recovered protected polypeptide is dried. Methods of drying are known to those skilled in the art, such as vacuum drying.

In the deprotecting step, Step (ii), of the process of the invention, an acid is added to the protected polypeptide which is formed in Step (i) to form a polypeptide or a pharmaceutically acceptable salt thereof. The acid cleaves the γ-p-methoxybenzyl group or γ-benzyl group from the glutamate moiety and the N-t-butoxycarbonyl group from the lysine moiety. In addition, the acid cleaves the amide bonds of the polypeptide or pharmaceutically acceptable salt thereof forming heterogenous polypeptide fragments.

In the deprotecting step, Step (b), of the process of the invention, an acid is added to the protected glatiramer formed in Step (a) to form a glatiramer. The acid cleaves the γ-p-methoxybenzyl group or the γ-benzyl group from the glutamate moiety and the N-t-butoxycarbonyl group from the lysine moiety. In addition, the acid cleaves the amide bonds of the glatiramer forming heterogenous glatiramer fragments.

Suitable acids include, but are not limited to, acetic acid, hydrochloric acid, hydrogen bromide, hydrogen fluoride, methane sulfonic acid, trifluoromethane sulfonic acid, phosphoric acid, trifluoroacetic acid and sulfuric acid. A mixture of acids may also be used. Preferred acids are selected from trifluoroacetic acid, a mixture of acetic acid and hydrochloric acid, a mixture of acetic acid and hydrogen bromide and a mixture of acetic acid and sulfuric acid. The acid may be added in the form of an aqueous solution.

The acid is preferably present in an amount of from about 0.1 wt. % to about 100 wt. %, more preferably from about 1 wt. % to about 10 wt. %, based on the weight of the protected polypeptide or protected glatiramer. Most preferably, the acid is present in an amount of from about 2 wt. % to about 6 wt. %, based on the weight of the protected polypeptide or protected glatiramer.

The temperature of the reaction medium during addition of the acid is preferably from about 10° C. to about 40° C., more preferably 15° C. to about 30° C. The acid is preferably added over a period of time from about 1 hour to about 30 hours, with stirring. Most preferably, the acid is added to the protected polypeptide or protected glatiramer at a temperature of about 25° C. for a period of from about 1 hour to about 8 hours, with stirring.

Excess acid is preferably removed from the reaction mixture by purging the reaction mixture with nitrogen, lyophilization, or by means of a rotary evaporator under vacuum to obtain a deprotected polypeptide in solid form. However, other separation techniques known to those skilled in the art may also be used.

The deprotected polypeptide or deprotected glatiramer in the form of a free base or acid addition salt is preferably dissolved in water or an aqueous acetic acid solution. Undesired low molecular weight polypeptide or glatiramer fragments, i.e., less than about 2 kDa, and high molecular weight polypeptide or glatiramer fragments, i.e., greater than about 40 kDa, are preferably removed by such methods as dialysis or diafiltration. Preferred membranes include Visking partially permeable cellulose membranes, such as a Size 6 membrane having a molecular weight cut-off of 12-14 kDa, available from Medicell International Ltd., and tangential flow filtration (TFF) membranes, such as a Pellicon XL PLCCC 10 (50 cm$^2$) or PLCCC 5 (50 cm$^2$), available from Millipore. In a preferred embodiment of the invention, the deprotected polypeptide or deprotected glatiramer is dissolved in water and subjected to dialysis, followed by dialysis in aqueous acetic acid solution.

The present inventors have determined that the desired molecular weight polypeptide or a pharmaceutically acceptable salt thereof may be controlled by dilution, concentration of the acid added in Step (ii) or Step (b), and/or time.

In one embodiment of the invention, water is removed from the deprotected polypeptide. A preferred method of removal is lyophilization. In lyophilization, the solution is frozen and placed under vacuum so that the water (ice) vaporizes in the vacuum (sublimes) without melting and the non-water components (deprotected polypeptide and residual salt) are left behind in an undamaged state, i.e., without chemical decomposition. The dried product of lyophilization contains the deprotected polypeptide and residual salt.

In one embodiment of the invention, the deprotected polypeptide is treated with glacial acetic acid to form glatiramer acetate salt. The glatiramer acetate salt is collected preferably by lyophilization to yield a glatiramer acetate salt product.

II. Phase Transfer Process.

In one embodiment of the invention, the process for preparing a polypeptide comprising L-tyrosine, L-alanine, L-glutamate and L-lysine, or a pharmaceutically acceptable salt thereof, comprises treating a protected polypeptide with an aqueous solution of an alkali or alkaline earth metal hydroxide to form a polypeptide or a pharmaceutically acceptable salt thereof.

In one embodiment of the invention, the process comprises:
(a)$^1$ polymerizing a mixture of N-carboxyanhydride of L-tyrosine, N-carboxyanhydride of L-alanine, N-carboxyanhydride of a protected L-glutamate and N-carboxyanhydride of a protected L-lysine, in a polar aprotic solvent in the presence of an initiator, to form a protected polypeptide; and
(b)$^1$ adding an aqueous solution of an alkali or alkaline earth metal hydroxide to the protected polypeptide formed in Step (a)$^1$ to form a polypeptide or a pharmaceutically acceptable salt thereof.

In one embodiment of the invention, the process comprises:
(a)$^{1'}$ polymerizing a mixture of N-carboxyanhydride of L-tyrosine, N-carboxyanhydride of L-alanine, N-carboxyanhydride of a γ-benzyl L-glutamate L-glutamate and N-carboxyanhydride of N$^ε$-trifluoroacetyl L-lysine, in a polar aprotic solvent in the presence of an initiator, to form a protected glatiramer;
(b)$^{1'}$ adding an aqueous solution of an alkali or alkaline earth metal hydroxide to the protected glatiramer formed in Step (a)$^{1'}$ to form a glatiramer; and
(c)$^{1'}$ treating the glatiramer with acetic acid to form glatiramer acetate.

In the deprotecting steps, Step (b)$^1$ and Step (b)$^{1'}$, of the process of the invention, an aqueous solution of an alkali or alkaline earth metal hydroxide is added to the protected polypeptide formed in Step (a)$^1$ or to the protected glatiramer formed in Step (a)$^{1'}$. In Step (b)$^1$ and Step (b)$^{1'}$, the protecting groups on the glutamic acid moiety, i.e., the γ-benzyl group, and the protecting groups on the lysine moiety, i.e., N$^ε$-trifluoroacetyl group, are removed. In addition, the alkali or alkaline earth metal hydroxide cleaves the amide bonds of the polypeptide or glatiramer forming heterogenous polypeptide or glatiramer fragments.

While not wishing to be bound by any particular theory, the present inventors believe that the removal of the protecting groups from the protected polypeptide or protected glatiramer results in a phase transfer of the deprotected polypeptide or deprotected glatiramer from the organic phase to the aqueous phase.

In the absence of a buffer in Step (b)$^1$ or Step (b)$^{1'}$, the pH during Step (b)$^1$ and Step (b)$^{1'}$, is generally about 13 to about 14 after the addition of the aqueous solution of an alkali or alkaline earth metal hydroxide. In the presence of a buffer in Step (b)$^1$ or Step (b)$^{1'}$, the pH is generally about 8 to about 12. The buffer may be added or formed in situ. A preferred buffer is an acetate buffer such as sodium acetate.

The alkali or alkaline earth metal hydroxide is preferably selected from calcium hydroxide, lithium hydroxide, magnesium hydroxide, potassium hydroxide and sodium hydroxide. More preferably, the alkali or alkaline earth metal hydroxide is sodium hydroxide. A combination of alkali or alkaline earth metal hydroxides may also be used.

The alkali or alkaline earth metal hydroxide is preferably present in an amount of from about 0.1 wt. % to about 400 wt. %, more preferably from about 10 wt. % to about 300 wt. %, based on the weight of the protected polypeptide or protected glatiramer. Most preferably, the alkali or alkaline earth metal hydroxide is present in an amount of from about 140 wt. % to about 260 wt. %, based on the weight of the protected polypeptide or protected glatiramer.

An aqueous solution of an alkali or alkaline earth metal hydroxide is added to the protected polypeptide or protected glatiramer preferably at a temperature of from about −78° C. to about 40° C., more preferably −25° C. to about 30° C., for a period of time preferably from about 1 hour to about 30 hours. Most preferably, an aqueous solution of an alkali or alkaline earth metal hydroxide is added to the protected polypeptide or protected glatiramer at a temperature from about −10° C. to about 10° C., e.g., 0° C., for a period of from about 1 hour to about 8 hours, with stirring. The addition of an aqueous solution of an alkali or alkaline earth metal hydroxide results in a phase separation wherein an organic phase and an aqueous phase are formed.

The organic phase substantially contains the polar aprotic solvent and the protected polypeptide or protected glatiramer. The aqueous phase substantially contains water, the alkali or alkaline earth metal hydroxide, and the deprotected polypeptide or deprotected glatiramer in the form of a free base. The aqueous phase and the organic phase are preferably separated by using a centrifuge and decanting the organic phase.

An additional advantage of the process of the invention is that the addition of the alkali or alkaline earth metal hydroxide causes deprotection of the protected polypeptide to form a deprotected polypeptide, or deprotection of the protected glatiramer to form a deprotected glatiramer. In addition, the alkali or alkaline earth metal hydroxide causes cleavage of the amide bonds in the deprotected polypeptide or deprotected glatiramer to form polypeptide or glatiramer fragments.

The aqueous phase is preferably treated with an organic or mineral acid to achieve a pH of about 7 to about 8. Such organic or mineral acids to adjust the pH are well-known to those skilled in the art and include, but are not limited to, acetic acid, formic acid, oxalic acid and hydrochloric acid. Dilute hydrochloric acid is preferred. The amount of organic or mineral acid used is preferably an equivalent amount based on the amount of the alkali or alkaline earth metal hydroxide added during Step $(b)^1$ or Step $(b)^{1'}$ which is sufficient to produce a pH of about 7 to about 8.

Undesired low molecular weight polypeptide or glatiramer fragments, i.e., less than about 2 kDa, and high molecular weight polypeptide or glatiramer fragments, i.e., greater than about 40 kDa, are preferably removed by such methods as dialysis or diafiltration. Preferred membranes include Visking partially permeable cellulose membranes such as a Size 6 membrane having a molecular weight cut-off of 12-14 kDa, available from Medicell International Ltd., and tangential flow filtration (TFF) membranes, such as a Pellicon XL PLCCC 10 (50 cm$^2$) or PLCCC 5 (50 cm$^2$), available from Millipore. In a preferred embodiment of the invention, the deprotected polypeptide or deprotected glatiramer is subjected to dialysis in water, followed by dialysis in aqueous acetic acid solution.

III. Process Using an Amine or Ammonia.

In one embodiment of the invention, the process comprises:

(a)$^2$ polymerizing a mixture of N-carboxyanhydride of L-tyrosine, N-carboxyanhydride of L-alanine, N-carboxyanhydride of a protected L-glutamate and N-carboxyanhydride of a protected L-lysine, in a polar aprotic solvent in the presence of an initiator, to form a protected polypeptide;

(b)$^2$ admixing an acid with the protected polypeptide formed in Step (a)$^2$ and a solvent, to form a product, preferably, the acid is admixed with a solution or suspension comprising the protected polypeptide and solvent; and (c)$^2$ admixing a substance selected from the group consisting of diisopropylamine, isopropylamine, ammonia, and mixtures thereof, with the product formed in Step (b)$^2$, and water or a mixture of a solvent and water, to form a deprotected polypeptide or a pharmaceutically acceptable salt thereof.

In one embodiment of the invention, the process comprises:

(a)$^{2'}$ polymerizing a mixture of N-carboxyanhydride of L-tyrosine, N-carboxyanhydride of L-alanine, N-carboxyanhydride of a protected L-glutamate and N-carboxyanhydride of a protected L-lysine, in a polar aprotic solvent in the presence of an initiator, to form a protected glatiramer, wherein said protected L-glutamate is selected from the group consisting of γ-p-methoxybenzyl L-glutamate, γ-benzyl L-glutamate and mixtures thereof;

(b)$^{2'}$ admixing an acid with the protected glatiramer formed in Step (a)$^{2'}$ and a solvent, to form a product;

(c)$^{2'}$ admixing a substance selected from the group consisting of diisopropylamine, isopropylamine, ammonia and mixtures thereof, with the product formed in Step (b)$^{2'}$, and water or a mixture of a solvent and water, to form a deprotected glatiramer; and (d)$^{2'}$ treating the deprotected glatiramer formed in Step (c)$^{2'}$ with acetic acid to form glatiramer acetate.

In the first deprotecting step, Step (b)$^2$ and Step (b)$^{2'}$ of the process of the invention, an acid is admixed with the protected polypeptide formed in Step (a)$^2$ or protected glatiramer formed in Step (a)$^{2'}$, and a solvent to form a product. Preferably, the acid is added to a mixture, i.e., a solution or suspension, comprising the protected polypeptide or protected glatiramer and a solvent. In Step (b)$^2$ and Step (b)$^{2'}$ the protecting groups on the glutamic acid moiety, i.e., γ-p-methoxybenzyl group and/or γ-benzyl group, are removed. While not wishing to be bound by any particular theory, the present inventors believe that the acid also cleaves amide bonds of the protected polypeptide or protected glatiramer forming heterogenous polypeptide or glatiramer fragments.

Suitable acids include, but are not limited to, acetic acid, hydrochloric acid, hydrogen bromide, hydrogen fluoride, methane sulfonic acid, trifluoromethane sulfonic acid, phosphoric acid, trifluoroacetic acid and sulfuric acid. A mixture of acids may also be used. Preferred acids are selected from trifluoroacetic acid, a mixture of acetic acid and hydrochloric acid, a mixture of acetic acid and hydrogen bromide and a mixture of acetic acid and sulfuric acid. The acid may be added in the form of an aqueous solution.

The acid is preferably present in an amount of from about 0.1 wt. % to about 100 wt. %, more preferably from about 1 wt. % to about 10 wt. %, based on the weight of the protected polypeptide or protected glatiramer. Most preferably, the acid is present in an amount of from about 2 wt. % to about 6 wt. %, based on the weight of the protected polypeptide or protected glatiramer.

The temperature of the reaction medium during addition of the acid is preferably from about 10° C. to about 40° C., more preferably 15° C. to about 30° C. The acid is preferably added over a period of time from about 1 hour to about 30 hours, with stirring. Most preferably, the acid is added to the protected polypeptide or protected glatiramer at a temperature of about 25° C. for a period of from about 1 hour to about 8 hours, with stirring.

The solvent used in the first deprotection step, Step (b)$^2$ and Step (b)$^{2'}$, is selected from polar protic solvents and polar aprotic solvents. Preferably, the solvent used in Step (b)$^2$ and Step (b)$^{2'}$ is selected from acetic acid, tetrahydrofuran, ethyl acetate, dimethyl furan, dimethylformamide, 1,4-dioxane, dimethoxyethane, 1,2-dichloroethylene, dimethylsulfoxide and dichloromethane. A mixture of solvents may also be used. Most preferably, the solvent used in Step (b)$^2$ and Step (b)$^{2'}$ is tetrahydrofuran or acetic acid.

The amount of solvent used in Step (b)$^2$ and Step (b)$^{2'}$ is preferably from about 1-fold (wt.) to about 1,000-fold (wt.), more preferably, from about 10-fold (wt.) to about 500-fold (wt.), based on the amount of protected polypeptide or protected glatiramer which is used in Step (b)$^2$ or Step (b)$^{2'}$.

In the second deprotecting step, Step $(c)^2$ and Step $(c)^{2'}$ of the process of the invention, a substance selected from the group consisting of diisopropylamine, isopropylamine, ammonia and mixtures thereof, is admixed with the product formed in Step $(b)^2$ or Step $(b)^{2'}$, and water or a mixture of a solvent and water, to form a deprotected polypeptide or deprotected glatiramer.

Preferably, the substance selected from the group consisting of diisopropylamine, isopropylamine, ammonia and mixtures thereof, is added to a mixture, i.e., a solution or suspension, comprising the product formed in Step $(b)^2$ or Step $(b)^{2'}$, and water or a mixture of a solvent and water. The ammonia is in the form of $NH_3$ (aqueous) or $NH_3$ (gas). Preferably an aqueous solution of ammonia is used having a pH of about 7 to about 14. The addition of a substance selected from the group consisting of diisopropylamine, isopropylamine, ammonia and mixtures thereof, to the product formed in Step $(b)^2$ or Step $(b)^{2'}$ preferably removes the protecting group, such as $N^\epsilon$-trifluoroacetyl group, of the lysine moiety. Preferably the deprotected polypeptide is a deprotected glatiramer in the form of a free base.

The substance selected from the group consisting of diisopropylamine, isopropylamine, ammonia and mixtures thereof, is preferably present in an amount of from about 1-fold (wt.) to about 1,000-fold (wt), more preferably from about 10-fold (wt.) to about 500-fold (wt), based on the total weight of the product of Step $(b)^2$ or Step $(b)^{2'}$ which is used in Step $(c)^2$ or Step $(c)^{2'}$. Most preferably, the substance selected from the group consisting of diisopropylamine, isopropylamine, ammonia and mixtures thereof, is present in an amount of from about 50-fold (wt.) to about 150-fold (wt).

The substance selected from the group consisting of diisopropylamine, isopropylamine, ammonia and mixtures thereof, is preferably admixed with a solution or suspension comprising the product formed in Step $(b)^2$ or Step $(b)^{2'}$, and water or a mixture of a solvent and water, at a temperature of from about 10° C. to about 60° C., more preferably 15° C. to about 40° C., for a period of time preferably from about 1 minute to about 60 hours, to form a deprotected polypeptide or deprotected glatiramer. Suitable solvents include, but are not limited to, tetrahydrofuran, ethyl acetate, dimethyl furan, dimethylformamide, 1,4-dioxane, dimethoxyethane, 1,2-dichloroethylene, dimethylsulfoxide and dichloromethane. A preferred solvent is tetrahydrofuran.

More preferably, the substance selected from the group consisting of diisopropylamine, isopropylamine, ammonia and mixtures thereof, is admixed with a solution or suspension comprising the product formed in Step $(b)^2$ or Step $(b)^{2'}$, and water or a mixture of a solvent and water, at a temperature of from about 20° C. to about 30° C., for a period of from about 1 hour to about 30 hours, to form a deprotected polypeptide or deprotected glatiramer. Unreacted diisopropylamine or ammonia, or any solvent or water, is preferably removed by evaporation or vacuum distillation.

Undesired low molecular weight polypeptide or glatiramer fragments, i.e., less than about 2 kDa, and high molecular weight polypeptide or glatiramer fragments, i.e., greater than about 40 kDa, are preferably removed by such methods as dialysis or diafiltration. Preferred membranes include Visking partially permeable cellulose membranes, such as a Size 6 membrane having a molecular weight cut-off of 12-14 kDa, available from Medicell International Ltd., and TFF membranes, such as a Pellicon XL PLCCC 10 (50 cm$^2$) or PLCCC 5 (50 cm$^2$), available from Millipore. In a preferred embodiment of the invention, the deprotected polypeptide or deprotected glatiramer is subjected to dialysis in water, followed by dialysis in aqueous acetic acid solution.

IV. Process Using an Alkali or Alkaline Earth Metal Hydroxide, Carbonate or Hydrogencarbonate.

In one embodiment of the invention, the process comprises:
(a)$^3$ polymerizing a mixture of N-carboxyanhydride of L-tyrosine, N-carboxyanhydride of L-alanine, N-carboxyanhydride of a protected L-glutamate and N-carboxyanhydride of a protected L-lysine, in a polar aprotic solvent in the presence of an initiator, to form a protected polypeptide;
(b)$^3$ admixing an acid with the protected polypeptide formed in Step (a)$^3$ and a solvent, to form a product, preferably, the acid is admixed with a solution or suspension comprising the protected polypeptide and solvent; and
(c)$^3$ admixing a substance selected from the group consisting of an alkali or alkaline earth metal hydroxide, a carbonate, a hydrogencarbonate and mixtures thereof, with the product formed in Step (b)$^3$, and a solvent or a mixture of a solvent and water, to form a deprotected polypeptide or a pharmaceutically acceptable salt thereof.

In one embodiment of the invention, the process comprises:
(a)$^{3'}$ polymerizing a mixture of N-carboxyanhydride of L-tyrosine, N-carboxyanhydride of L-alanine, N-carboxyanhydride of a protected L-glutamate and N-carboxyanhydride of $N^\epsilon$-trifluoroacetyl L-lysine, in a polar aprotic solvent in the presence of an initiator, to form a protected glatiramer, wherein said protected L-glutamate is selected from the group consisting of γ-p-methoxybenzyl L-glutamate, γ-benzyl L-glutamate and mixtures thereof;
(b)$^{3'}$ admixing an acid with a mixture comprising the protected glatiramer formed in Step (a)$^3$ and a solvent, to form a product;
(c)$^{3'}$ admixing a substance selected from the group consisting of an alkali or alkaline earth metal hydroxide, a carbonate, a hydrogencarbonate and mixtures thereof, with a mixture comprising the product formed in Step (b)$^{3'}$, and a solvent or a mixture of a solvent and water, to form a deprotected glatiramer; and
(d)$^{3'}$ treating the deprotected glatiramer formed in Step (c)$^{3'}$ with acetic acid to form glatiramer acetate.

In the first deprotecting step, Step (b)$^3$ and Step (b)$^{3'}$ of the process of the invention, an acid is admixed with the protected polypeptide formed in Step (a)$^3$ or protected glatiramer formed in Step (a)$^{3'}$, and a solvent to form a product. Preferably, the acid is added to a mixture, i.e., a solution or suspension, comprising the protected polypeptide or protected glatiramer and a solvent. In Step (b)$^3$ and Step (b)$^{3'}$ the protecting groups on the glutamic acid moiety, i.e., γ-p-methoxybenzyl group and/or γ-benzyl group, are removed. While not wishing to be bound by any particular theory, the present inventors believe that the acid also cleaves amide bonds of the protected polypeptide or protected glatiramer forming heterogenous polypeptide fragments.

Suitable acids include, but are not limited to, acetic acid, hydrochloric acid, hydrogen bromide, hydrogen fluoride, methane sulfonic acid, trifluoromethane sulfonic acid, phosphoric acid, trifluoroacetic acid and sulfuric acid. A mixture of acids may also be used. Preferred acids are selected from trifluoroacetic acid, a mixture of acetic acid and hydrochloric acid, a mixture of acetic acid and hydrogen bromide and a mixture of acetic acid and sulfuric acid. The acid may be added in the form of an aqueous solution.

The acid is preferably present in an amount of from about 0.1 wt. % to about 100 wt. %, more preferably from about 1 wt. % to about 10 wt. %, based on the weight of the protected polypeptide or protected glatiramer. Most preferably, the acid is present in an amount of from about 2 wt. % to about 6 wt. %, based on the weight of the protected polypeptide or protected glatiramer.

The temperature of the reaction medium during addition of the acid is preferably from about 10° C. to about 40° C., more preferably 15° C. to about 30° C. The acid is preferably added over a period of time from about 1 hour to about 30 hours, with stirring. Most preferably, the acid is added to the protected polypeptide or protected glatiramer at a temperature of about 25° C. for a period of from about 1 hour to about 8 hours, with stirring.

The solvent used in the first deprotection step, Step $(b)^3$ and Step $(b)^{3'}$, is selected from polar protic solvents and polar aprotic solvents. Preferably, the solvent used in Step $(b)^3$ and Step $(b)^{3'}$ is selected from acetic acid, tetrahydrofuran, ethyl acetate, dimethyl furan, dimethylformamide, 1,4-dioxane, dimethoxyethane, 1,2-dichloroethylene, dimethylsulfoxide and dichloromethane. A mixture of solvents may also be used. Most preferably, the solvent used in Step $(b)^2$ and Step $(b)^{2'}$ is tetrahydrofuran or acetic acid.

The amount of solvent used in Step $(b)^3$ and Step $(b)^{3'}$ is preferably from about 1-fold (wt.) to about 1,000-fold (wt.), more preferably, from about 10-fold (wt.) to about 500-fold (wt.), based on the amount of protected polypeptide or protected glatiramer which is used in Step $(b)^3$ or Step $(b)^{3'}$ In the second deprotecting step, Step $(c)^3$ and Step $(c)^{3'}$, of the process of the invention, a substance selected from the group consisting of an alkali or alkaline earth metal hydroxide, a carbonate, a hydrogencarbonate and mixtures thereof, is admixed with the product formed in Step $(b)^3$ or Step $(b)^{3'}$, and water or a mixture of a solvent and water, to form a deprotected polypeptide or deprotected glatiramer.

Preferably, the substance selected from the group consisting of an alkali or alkaline earth metal hydroxide, a carbonate, a hydrogencarbonate and mixtures thereof, is added to a mixture, i.e., a solution or suspension, comprising the product formed in Step $(b)^3$ or Step $(b)^{3'}$, and water or a mixture of a solvent and water. The addition of a substance selected from the group consisting of an alkali or alkaline earth metal hydroxide, a carbonate, a hydrogencarbonate and mixtures thereof, to the product formed in Step $(b)^3$ or Step $(b)^{3'}$ preferably removes the $N^\epsilon$-trifluoroacetyl group of the lysine moiety. Preferably the deprotected polypeptide is a deprotected glatiramer in the form of a free base.

The substance selected from the group consisting of an alkali or alkaline earth metal hydroxide, a carbonate and a hydrogencarbonate, and includes calcium hydroxide, lithium hydroxide, magnesium hydroxide, potassium hydroxide, barium hydroxide, sodium hydroxide, calcium carbonate, lithium carbonate, magnesium carbonate, potassium carbonate, sodium carbonate, calcium hydrogencarbonate, lithium hydrogencarbonate, magnesium hydrogencarbonate, potassium hydrogencarbonate and sodium hydrogencarbonate. More preferably, the substance used in Step $(c)^3$ or Step $(c)^{3'}$ is selected from the group consisting of sodium hydroxide, lithium hydroxide and potassium hydroxide.

The substance selected from the group consisting of an alkali or alkaline earth metal hydroxide, a carbonate, a hydrogencarbonate and mixtures thereof, is preferably present in an amount of from about 1-fold (wt.) to about 1,000-fold (wt), more preferably from about 10-fold (wt.) to about 500-fold (wt), based on the total weight of the product of Step $(b)^3$ or Step $(b)^{3'}$ which is used in Step $(c)^3$ or Step $(c)^{3'}$. Most preferably, the substance selected from the group consisting of an alkali or alkaline earth metal hydroxide, a carbonate, a hydrogencarbonate and mixtures thereof, is present in an amount of from about 50-fold (wt.) to about 150-fold (wt).

The substance selected from the group consisting of an alkali or alkaline earth metal hydroxide, a carbonate, a hydrogencarbonate and mixtures thereof, is preferably admixed with a solution or suspension comprising the product formed in Step $(b)^3$ or Step $(b)^{3'}$, and water or a mixture of a solvent and water, at a temperature of from about 10° C. to about 60° C., more preferably 15° C. to about 40° C., for a period of time preferably from about 1 minute to about 60 hours, to form a deprotected polypeptide or deprotected glatiramer. Suitable solvents include, but are not limited to, tetrahydrofuran, ethyl acetate, dimethyl furan, dimethylformamide, 1,4-dioxane, dimethoxyethane, 1,2-dichloroethylene, dimethylsulfoxide and dichloromethane. A preferred solvent is tetrahydrofuran.

More preferably, the substance selected from the group consisting of an alkali or alkaline earth metal hydroxide, a carbonate, a hydrogencarbonate and mixtures thereof, is admixed with a solution or suspension comprising the product formed in Step $(b)^3$ or Step $(b)^{3'}$, and water or a mixture of a solvent and water, at a temperature of from about 20° C. to about 30° C., for a period of from about 1 hour to about 30 hours, to form a deprotected polypeptide or deprotected glatiramer. Unreacted alkali or alkaline earth metal hydroxide, carbonate, hydrogencarbonate or any solvent or water, is preferably removed by evaporation or vacuum distillation.

The amount of solvent or a mixture of a solvent and water which is used in Step $(c)^3$ or Step $(c)^{3'}$ is preferably from about 1-fold (wt.) to about 1,000-fold (wt.), more preferably, from about 10-fold (wt.) to about 500-fold (wt.), based on the total weight of the product of Step $(b)^3$ or Step $(b)^{3'}$ which is used in Step $(c)^3$ or Step $(c)^{3'}$.

After the second deprotection step, Step $(c)^3$ and Step $(c)^{3'}$, any layers are separated preferably in separatory funnel, or the solvent is preferably removed by evaporation or vacuum distillation. The deprotected polypeptide or deprotected glatiramer is preferably obtained as a solution in water.

Undesired low molecular weight polypeptide or glatiramer fragments, i.e., less than about 2 kDa, and high molecular weight polypeptide or glatiramer fragments, i.e., greater than about 40 kDa, are preferably removed by such methods as dialysis or diafiltration. Preferred membranes include Visking partially permeable cellulose membranes, such as a Size 6 membrane having a molecular weight cut-off of 12-14 kDa, available from Medicell International Ltd., and TFF membranes, such as a Pellicon XL PLCCC 10 (50 cm$^2$) or PLCCC 5 (50 cm$^2$), available from Millipore. In a preferred embodiment of the invention, the deprotected polypeptide or deprotected glatiramer is subjected to dialysis in water, followed by dialysis in aqueous acetic acid solution.

The weight average molecular weight of the polypeptide or a pharmaceutically acceptable salt thereof which is prepared in accordance with the processes of the invention is preferably from about 2 kDa to about 30 kDa, more preferably from about 4.7 Da to about 11 kDa, and most preferably from about 7 kDa to about 10 kDa, as determined by gas permeation chromatography (GPC). Preferably, the polypeptide or pharmaceutically acceptable salt thereof is substantially free of polypeptide fragments having a molecular weight of greater than about 40 kDa. Preferably, the polypeptide or pharmaceutically acceptable salt thereof is substantially free of polypeptide fragments having a molecular weight of less than about 2 kDa. As used herein, "substantially free" means less than about 5% by weight, more preferably less than about 2.5% by weight of the polypeptide prepared according to the process of the invention.

The polypeptide or pharmaceutically acceptable salt thereof, preferably glatiramer acetate, prepared according to the process of the invention may be formulated by conventional methods known in the art.

In one embodiment of the invention, the polypeptide or pharmaceutically acceptable salt thereof, which is prepared by the process of the invention, is dissolved or suspended in an acceptable pharmaceutical liquid vehicle, such as water, and the solution or suspension is injected into the body.

In one embodiment of the invention, the glatiramer acetate salt is dissolved in a mixture containing water and mannitol, and the solution is injected into the body.

Typically, the polypeptide or a pharmaceutically acceptable salt thereof is administered daily to patients suffering from multiple sclerosis, e.g., at a dosage of 20 mg of glatiramer acetate.

The following non-limiting examples illustrate further aspects of the invention. Examples 1-7 relate to an acid hydrolysis process for preparing glatiramer acetate.

Example 1

Preparation of a Protected Polypeptide

N-Carboxyanhydride of L-alanine (860 mg, 7.5 mmol), N-carboxyanhydride of γ-benzyl L-glutamate (600 mg, 2.3 mmol), N-carboxyanhydride of N-t-butoxycarbonyl L-lysine (1410 mg, 5.2 mmol) and N-carboxyanhydride of L-tyrosine (300 mg, 1.4 mmol) are placed in a three-neck flask. Distilled anhydrous dioxane (57 mL) is added. Diethylamine (3.4 µL) is added. The resulting mixture is stirred mechanically for 24 hours at a temperature of approximately 22-25° C. The mixture is slowly poured into 100 mL deionized water and filtered under vacuum. The solid is kept under vacuum for 12 hours.

Example 2

Preparation of a Protected Polypeptide

N-Carboxyanhydride of L-alanine (430 mg, 3.75 mmol), N-carboxyanhydride of γ-benzyl L-glutamate (300 mg, 1.15 mmol), N-carboxyanhydride of N-t-butoxycarbonyl L-lysine (705 mg, 2.6 mmol) and N-carboxyanhydride of L-tyrosine (150 mg, 0.7 mmol) are placed in a three-neck flask. Distilled anhydrous dioxane (28.5 mL) is added. Diethylamine (1.7 µL) is added. The resulting mixture is stirred mechanically for 24 hours at a temperature of approximately 22-25° C. The mixture is slowly poured into 100 mL deionized water and filtered under vacuum. The solid is kept under vacuum for 12 hours.

Example 3

Deprotecting the Protected Polypeptide Prepared in Example 1 with HBr/Acetic Acid The protected polypeptide prepared in Example 1 (200 mg) is suspended in 7 mL of 33% hydrogen bromide in acetic acid. The starting material slowly dissolves forming a red brown solution. The mixture is stirred for 17 hours at a temperature of approximately 22° C. The solution of HBr/acetic acid is evaporated to dryness using a rotary evaporator under reduced pressure. To this residue, 100 mL of water is added to dissolve the solid. The solution is placed in a Visking partially permeable cellulose membrane which is in the form of a tube, Size 6, having a molecular weight cut-off of 12-14 kDa. Size 6 tube has a diameter of $^{27}/_{32}$ inches, 21.5 mm and a width of 32-34 mm. The tube is available from Medicell International Ltd. The tube containing the solution is stirred in a beaker of water. Polypeptide fragments having a molecular weight less than about 2 kDa are removed by osmosis from the dialysis tube. The tube is removed from the water and stirred in a beaker containing 0.3% acetic acid in water. The resulting product is removed from the tube and lyophilized to obtain glatiramer acetate as a pure white solid.

Example 4

Deprotecting the Protected Polypeptide Prepared in Example 1 with HCl/Acetic Acid The protected polypeptide prepared in Example 1 (200 mg) is suspended in 20 mL of a mixture prepared of 9.4 mL concentrated hydrochloric acid adjusted to 20 mL with glacial acetic acid. The starting material slowly dissolves forming a slightly turbid solution. The mixture is stirred for 17 hours at a temperature of approximately 22° C. The solution of HCl/acetic acid is evaporated to dryness using a rotary evaporator under reduced pressure. To this residue, 100 mL of water is added to dissolve the solid. The solution is placed in a Visking partially permeable cellulose membrane which is in the form of a tube, Size 6, having a molecular weight cut-off of 12-14 kDa. Size 6 tube has a diameter of $^{27}/_{32}$ inches, 21.5 mm and a width of 32-34 mm. The tube is available from Medicell International Ltd. The tube containing the solution is stirred in a beaker of water. Polypeptide fragments having a molecular weight less than about 2 kDa are removed by osmosis from the dialysis tube. The tube is removed from the water and stirred in a beaker containing 0.3% acetic acid in water. The resulting product is removed from the tube and lyophilized to obtain glatiramer acetate as a pure white solid.

Example 5

Deprotecting the Protected Polypeptide Prepared in Example 2 with HCl/Acetic Acid The protected polypeptide prepared in Example 2 (200 mg) is suspended in 20 mL of a mixture prepared of 9.4 mL concentrated hydrochloric acid adjusted to 20 mL with glacial acetic acid. The starting material slowly dissolves forming a slightly turbid solution. The mixture is stirred for 17 hours at a temperature of approximately 22° C. The solution of HCl/acetic acid is evaporated to dryness using a rotary evaporator under reduced pressure. To this residue, 100 mL of water is added to dissolve the solid. The solution is placed in a Visking partially permeable cellulose membrane which is in the form of a tube, Size 6, having a molecular weight cut-off of 12-14 kDa. Size 6 tube has a diameter of $^{27}/_{32}$ inches, 21.5 mm and a width of 32-34 mm. The tube is available from Medicell International Ltd. The tube containing the solution is stirred in a beaker of water. Polypeptide fragments having a molecular weight less than about 2 kDa are removed by osmosis from the dialysis tube. The tube is removed from the water and stirred in a beaker containing 0.3% acetic acid in water. The resulting product is removed from the tube and lyophilized to obtain glatiramer acetate as a pure white solid.

Example 6

Relative molecular weight determination by GPC using a UV Detector.
GPC-UV Detector Conditions:
Eluent: Phosphate buffer 0.05 M, pH 7.4, 5.6 g $Na_2HPO_4$, 116 g NaCl/4 L water
Column: PSS Suprema, 10 µm, 100 A, 8×300 mm.
Temperature: 23° C.
Pump: TSP AS 3000 autosampler
Inj.-Vol.: 50 µL
Concentration: about 2.0 mg/mL
Detector: TSP UV2000 at 276 nm
GPC-Software: PSS WinGPC Vers. 7.2
Samples: COPAXONE® (Lot #5308036) wherein the mannitol has been removed by dialysis
  COPAXONE® (Lot #8040341) wherein the mannitol has been removed by dialysis
  Sample A is glatiramer acetate prepared in Example 4 according to the process of the invention
  Sample B is glatiramer acetate prepared in Example 5 according to the process of the invention
Sample Preparation: The weighted samples are dispersed in the eluent and allowed to stand for full hydration at room temperature for about 12 hours. The sample solution is filtered through a 1.0 filter unit (Schleicher & Schuell)
The test results for GPC are summarized in Table I.

TABLE I

| Sample | $M_w$ [kD] |
|---|---|
| COPAXONE ®(Lot # 5308036) | 7.923 |
| COPAXONE ®(Lot # 8040341) | 9.524 |
| Sample A | 8.551 |
| Sample B | 7.689 |

The test results in Table I clearly show that the weight average molecular weight of glatiramer acetate prepared by the process of the invention, Samples A and B, is 8.551 kDa and 7.689 kDa, respectively, and the weight average molecular weight of COPAXONE® is 7.923 kDa and 9.524 kDa, depending on the lot number.

Example 7

Relative molecular weight determination by gel permeation chromatography (GPC) using a refractive index detector.

GPC-RI Detector Conditions:
Eluent: Phosphate buffer 0.05 M, pH 7.4, 5.6 g $Na_2HPO_4$, 116 g NaCl/4 L water
Column: PSS Suprema, 10 µm, 100 A, 8×300 mm
Temperature: 23° C.
Pump: TSP AS 3000 autosampler
Inj.-Vol.: 50 µL
Concentration: about 2.0 mg/mL
Detector: Shodex RI 71
GPC-Software: PSS WinGPC Vers. 7.2
Samples: COPAXONE® (Lot #5308036) wherein the mannitol has been removed by dialysis
  COPAXONE® (Lot #8040341) wherein the mannitol has been removed by dialysis
  Sample A is glatiramer acetate prepared in Example 4 according to the process of the invention
  Sample B is glatiramer acetate prepared in Example 5 according to the process of the invention
Sample Preparation: The weighted samples are dispersed in the eluent and allowed to stand for full hydration at room temperature for about 12 hours. The sample solution is filtered through a 1.0 filter unit (Schleicher & Schuell)
The test results for GPC with RI detector are summarized in Table II.

TABLE II

| Sample | $M_w$ [kD] |
|---|---|
| COPAXONE ®(Lot # 5308036) | 8.663 |
| COPAXONE ®(Lot # 8040341) | 9.641 |
| Sample A | 9.581 |
| Sample B | 8.224 |

The test results in Table II clearly show that the weight average molecular weight of glatiramer acetate prepared by the process of the invention, Samples A and B, is 9.581 kDa and 8.224 kDa, respectively, and the weight average molecular weight of COPAXONE® is 8.663 kDa and 9.641 kDa, depending on the lot number.

Examples 8-17 relate to a phase transfer process for preparing glatiramer acetate.

The present inventors have established a scale of 1 (low) to 5 (high) to quantify the influence of the alkaline compound (sodium hydroxide) on glatiramer formation. The test results are summarized in Table III.

TABLE III

| NaOH Conc. in 15 mL THF + 75 mg Glatiramer Free Base | Phase Separation | Recovery of Desired Molecular Weight Product from Aqueous Phase SM = 75 mg | Low Molecular Weight Polypeptide Formation | Product with Desired Molecular Weight Cut-off |
|---|---|---|---|---|
| 0.1 N/5 mL | No | 1 | 1 | 1 |
| 0.25 N/5 mL | 1 | 5 | 1 | 5 |
| 0.25 N/10 mL | 1 | 5 | 1 | 5 |
| 0.5 N/5 mL | 3 | 3 | 2 | 4 |
| 0.5 N/10 mL | 4 | 3 | 3 | 3 |
| 0.5 N/10 mL + 10 mL water | 5 | 3 | 2 | 4 |
| 1.0 N/5 mL | 5 | 3 | 5 | 1 |

The results in Table III clearly show that 0.1-1.0 N sodium hydroxide solutions may be used to prepare the polypeptide or a pharmaceutically acceptable salt thereof products of the invention. The results in Table III also show that the use of a sodium hydroxide concentration of at least 0.25 N is preferred to facilitate phase separation of the organic phase and aqueous phase.

Example 8

Polymerization Step (a)

N-Carboxyanhydride of tyrosine (30 mg, 0.010 mm), N-carboxyanhydride of alanine (62 mg, 0.054 mm), N-carboxyanhydride of γ-benzyl glutamate (42 mg, 0.016 mm) and N-carboxyanhydride of E-N-trifluoroacetyllysine (100 mg, 0.037 mm), are placed in a single-neck flask with a magnetic stirrer. To this mixture is added 20 mL of dry tetrahydrofuran. A clear solution is obtained. Diethylamine (10 μL) is added. The resulting mixture is stirred for 48 hours. The tetrahydrofuran is removed by evaporation. Water (150 mL) is added to the residue and the stirring is continued. A white solid is obtained. The solid is filtered and dried in a dessicator under vacuum.

The yield is determined to be 154 mg.

Example 9

Deprotecting Step (b)

Protected glatiramer acetate, 75 mg, prepared in Example 8 is transferred to a single-neck flask provided with a magnetic stirrer. Tetrahydrofuran (15 mL) is added to the flask and stirred. A clear solution is obtained. Aqueous solution of sodium hydroxide (8 mL) 0.5 N, is added. The addition of the sodium hydroxide solution results in the mixture becoming hazy. The mixture is stirred for 1 hour at 24-26° C. The formation of two phases is observed. The bottom layer is separated and acidified using dilute aqueous 1 N HCl solution to pH=6.0 with stirring. The crude glatiramer free base solution is filtered using a nylon filter (0.2 micron Nylon Acrodisk).

Example 10

Protected glatiramer acetate, 75 mg, prepared in Example 8 is transferred to a single-neck flask provided with a magnetic stirrer. Tetrahydrofuran (15 mL) is added to the flask and stirred. A clear solution is obtained. Aqueous solution of sodium hydroxide (10 mL) 0.25 N is added. The addition of the sodium hydroxide solution results in the mixture becoming hazy. The mixture is stirred for 16 hours at 25-26° C. The reaction mixture is centrifuged for 15 minutes. The formation of two phases is observed. The bottom layer is separated and acidified using dilute aqueous HCl solution to pH=7-7.5 with stirring. Stirring is continued for an additional 30 minutes and the pH is determined to be pH=8.0. The crude glatiramer free base solution is filtered.

Example 11

Polymerization Step

N-Carboxyanhydride of tyrosine (30 mg, 0.010 mm), N-carboxyanhydride of alanine (62 mg, 0.054 mm), N-carboxyanhydride of γ-benzyl glutamate (42 mg, 0.016 mm) and N-carboxyanhydride of E-N-trifluoroacetyllysine (100 mg, 0.037 mm), are placed in a single-neck flask with a magnetic stirrer. To this mixture is added 20 mL of dry dioxane. A clear solution is obtained. Diethylamine (10 μL) is added. The resulting mixture is stirred for 48 hours. To this, water (150 mL) is added slowly with stirring. A white solid is obtained. The solid is filtered and dried in a dessicator under vacuum.

The yield is determined to be 170 mg.

Example 12

Deprotecting Step

Protected glatiramer acetate, 75 mg, prepared in Example 11 is transferred to a single-neck flask provided with a magnetic stirrer. Dioxane (15 mL) is added to the flask and stirred. A clear solution is obtained. Aqueous solution of sodium hydroxide (10 mL) 0.5 N, is added. The addition of the sodium hydroxide solution results in the mixture becoming hazy. The mixture is stirred for 16 hours at 25-26° C. The reaction mixture is centrifuged for 15 minutes. The formation of two phases is observed. The bottom layer is separated and acidified using dilute aqueous HCl solution to pH=7-7.5 with stirring. Stirring is continued for an additional 30 minutes and the pH is determined to be pH=8.0. The crude glatiramer free base solution is filtered.

Example 13

Deprotecting Step Conducted at Lower Temperature

Protected glatiramer acetate, 75 mg, prepared in Example 12 is transferred to a single-neck flask provided with a magnetic stirrer. Tetrahydrofuran (15 mL) is added to the flask and the temperature of the solution is reduced to 0° C. Aqueous solution of sodium hydroxide (10 mL) 0.5 N, is added to the solution while maintaining a temperature of 0° C. The addition of the sodium hydroxide results in the solution becoming hazy. The solution is stirred for 3 hours at 0° C. The formation of two phases is observed. The bottom layer is separated and acidified using dilute aqueous HCl solution to pH=7-7.5 with stirring at 0° C. Stirring is continued for an additional 30 minutes and the pH is determined to be approximately pH=8.0. The crude glatiramer free base solution is filtered.

Example 14

Deprotecting Step with Acetate Buffer

Protected glatiramer acetate, 75 mg, prepared in Example 12 is transferred to a single-neck flask provided with a magnetic stirrer. Tetrahydrofuran (15 mL) is added to the flask and the temperature of the solution is reduced to 0° C. Aqueous solution of sodium hydroxide (10 mL) 0.5 N, and acetic acid (2 mL) is added to the solution while maintaining a temperature of 0° C. and a pH=12. The addition of the sodium hydroxide and acetic acid results in the solution becoming hazy. The solution is stirred for 3 hours at 0° C. The formation of two phases is observed. The bottom layer is separated and acidified using dilute aqueous HCl solution to pH=7-7.5 with stirring at 0° C. Stirring is continued for an additional 30 minutes and the pH is determined to be approximately pH=8.0. The crude glatiramer free base solution is filtered.

Example 15

Protected glatiramer acetate, 75 mg, prepared in Example 8 is transferred to a single-neck flask provided with a magnetic stirrer. Dioxane (15 mL) is added to the flask and stirred. A clear solution is obtained. Aqueous solution of sodium hydroxide (10 mL) 0.25 N is added. The addition of the sodium hydroxide solution results in the mixture becoming hazy. The mixture is stirred for 16 hours at 25-26° C. The reaction mixture is centrifuged for 15 minutes. The formation of two phases is observed. The bottom layer is separated and acidified using dilute aqueous HCl solution to pH=7-7.5 with stirring. Stirring is continued for an additional 30 minutes and the pH is determined to be pH=8.0. The crude glatiramer free base solution is filtered.

Example 16

Diafiltration

Tangential Flow Filtration

The crude glatiramer free base solution prepared in Example 9 is diluted to 120 with water. The dilute solution is first filtered through a 10 K diafiltration membrane, Pellicon XL, PLCCC 10 (50 cm$^2$), available from Millipore, and then, filtered through a 10 K diafiltration membrane, Pellicon XL, PLCCC 5 (50 cm$^2$), available from Millipore. The concentrated solution obtained is lyophilized. A white powder is obtained.

Example 17

Chromatographic Method of Purification of Glatirimer Acetate

The crude glatiramer free base solution prepared in Example 9 is subjected to chromatographic separation. A column for gel filtration, FRACTOGEL TSK HW55 (600×26 mm) is prepared in a Superformance 26 Merck cartridge according to the manufacturer's instructions. The column is equilibrated with 0.2M ammonium acetate buffer pH 5.0, 30 mL of glatiramer free base solution samples (20 mg/mL, in 0.2 M ammonium acetate pH 5.0) are loaded on the column and fractions are collected every 10 minutes. A fraction having an average molecular weight of 7-8 KDa is isolated.

Examples 18-25 relate to a process for preparing glatiramer acetate using an alkali or alkaline earth metal hydroxide, carbonate, or a hydrogen carbonate.

Example 16

Preparation of a Protected Polypeptide

N-Carboxyanhydride of L-tyrosine (207.19 mg, 1.0 mM), N-carboxyanhydride of L-alanine (620 mg, 5.4 mM), N-carboxyanhydride of γ-benzyl L-glutamate (430 mg, 1.6 mM) and N-carboxyanhydride of N$^\epsilon$-trifluoroacetyl L-lysine (1.01 g, 3.73 mM), are placed in a single-neck flask (100 mL) with a magnetic stirrer. To this mixture is added 40 mL of tetrahydrofuran. Diethylamine (10 μL) is added. The resulting mixture is stirred for 24 hours at a temperature of approximately 25° C. The mixture is slowly poured into 100 mL water while stirring. A solid is precipitated. The solid is filtered after 2 hours of stirring and washed with water. The solid is resuspended in 100 mL water and filtered. The solid is kept under vacuum for approximately 12 hours.

Example 19

Preparation of a Protected Polypeptide

N-Carboxyanhydride of L-tyrosine (207.19 mg, 1.0 mM), N-carboxyanhydride of L-alanine (620 mg, 5.4 mM), N-carboxyanhydride of γ-benzyl L-glutamate (430 mg, 1.6 mM) and N-carboxyanhydride of N$^\epsilon$-trifluoroacetyl L-lysine (1.01 g, 3.73 mM), are placed in a single-neck flask (100 mL) with a magnetic stirrer. To this mixture is added 40 mL of dioxane. Diethylamine (10 μL) is added. The resulting mixture is stirred for 48 hours at a temperature of approximately 25° C. The mixture is slowly poured into 100 mL water while stirring. A solid is precipitated. The solid is filtered and washed with water. The solid is resuspended in 100 mL water and filtered. The solid is kept under vacuum for approximately 12 hours.

Example 20

Cleavage of γ-Benzyl Moiety from the Polypeptide Prepared in Example 2

The protected polypeptide prepared in Example 19, 100 mg, is suspended in tetrahydrofuran (20 mL) and cooled in an ice water bath. Concentrated sulfuric acid, 4 mL, is added. The resulting clear solution is stirred for 20 hours at a temperature of approximately 25° C. The solvent, tetrahydrofuran, is removed by evaporation at 25° C. to form a viscous liquid. Water, 50 mL, is added to the viscous liquid with stirring. A white precipitate forms which is filtered under vacuum and dried over phosphorous pentoxide under vacuum at 25° C. for approximately 12 hours in the dark. A white solid is obtained. The solid is filtered and dried in a dessicator under vacuum. The yield is determined to be 75 mg.

Example 21

Cleavage of N$^\epsilon$-Trifluoroacetyl Moiety from the Polypeptide Prepared in Example 20

The protected polypeptide prepared in Example 20, 75 mg, is dispersed in 12 mL of tetrahydrofuran, 4 mL of 0.5 M aqueous sodium hydroxide is added with stirring. The mixture is stirred for 3 hours at ambient temperature (approximately 22° C.). The lower aqueous layer is separated and acidified with acetic acid to pH=6.0.

Example 22

Cleavage of γ-Benzyl Moiety from the Polypeptide Prepared in Example 19

The protected polypeptide prepared in Example 19, 1 g, is suspended in 50 mL of a mixture prepared of 47 mL concentrated HCl adjusted to 100 mL with glacial acetic acid. The starting material slowly dissolves forming a slightly turbid solution. The mixture is stirred for 18 hours at a temperature of approximately 22° C. The solution is poured into 1,000 mL of stirred water. A white precipitate is formed. The suspension is stirred for another 3 hours and then filtered. The product is washed with water and dried under vacuum at 50° C. for approximately 17 hours.

Example 23

Cleavage of N$^\epsilon$-Trifluoroacetyl Moiety from the Polypeptide Prepared in Example 22

The protected polypeptide prepared in Example 22, 300 mg, is dispersed in 45 mL of tetrahydrofurane, 25 mL of 0.5 M aqueous sodium hydroxide is added with stirring. The mixture is stirred for 3 hours at ambient temperature (approximately 22° C.). A clear, two-phase liquid system is formed. The lower aqueous layer is separated and acidified with acetic acid to pH=6.0. The clear, colorless solution is filled into dialysis bags and dialyzed at ambient temperature once against 0.3% aqueous acetic acid, and then against water until a pH of 5.5 is reached. This solution is filtered and lyophilized to yield glatiramer acetate as a white solid.

Example 24

Diafiltration

Tangential Flow Filtration

The glatiramer acetate solution prepared in Example 21 is adjusted to 120 mL with water to provide a 0.5-0.6 mg/mL concentration of the glatiramer acetate. The dilute solution is first filtered through a 30 K diafiltration membrane, Pellicon XL, PLCCC 10 (50 cm$^2$), available from Millipore, and then, filtered through a 3 K diafiltration membrane, Pellicon XL, PLCCC 5 (50 cm$^2$), available from Millipore. The concentrated solution obtained is lyophilized to provide glatiramer acetate in solid form.

Example 25

Chromatographic Method of Purification of Glatiramer Acetate

The glatiramer as extract of pH=6 prepared in Example 23 is concentrated in vacuo to dryness and subjected to chromatographic separation. A column for gel filtration, FRAC-TOGEL TSK HW55 (600×26 mm) is prepared in a Superformance 26 Merck cartridge according to the manufacturer's instructions. The column is equilibrated with 0.2 M ammonium acetate buffer pH 5.0, 30 mL of glatiramer free base solution samples (20 mg/mL, in 0.2 M ammonium acetate pH 5.0) are loaded on the column and fractions are collected. A fraction having an average molecular weight of 7-10 kDa is isolated.

Examples 26-33 relate to a process for preparing glatiramer acetate using an amine or ammonia.

Example 26

Preparation of a Protected Polypeptide

N-Carboxyanhydride of L-tyrosine (207.19 mg, 1.0 mM), N-carboxyanhydride of L-alanine (620 mg, 5.4 mM), N-carboxyanhydride of γ-benzyl L-glutamate (430 mg, 1.6 mM) and N-carboxyanhydride of N$^ε$-trifluoroacetyl L-lysine (1.01 g, 3.73 mM), are placed in a single-neck flask (100 mL) with a magnetic stirrer. To this mixture is added 40 mL of tetrahydrofuran. Diethylamine (10 µL) is added. The resulting mixture is stirred for 24 hours at a temperature of approximately 25° C. The mixture is slowly poured into 100 mL water while stirring. A solid is precipitated. The solid is filtered after 2 hours of stirring and washed with water. The solid is resuspended in 100 mL water and filtered. The solid is kept under vacuum for approximately 12 hours.

Example 27

Preparation of a Protected Polypeptide

N-Carboxyanhydride of L-tyrosine (207.19 mg, 1.0 mM), N-carboxyanhydride of L-alanine (620 mg, 5.4 mM), N-carboxyanhydride of γ-benzyl L-glutamate (430 mg, 1.6 mM) and N-carboxyanhydride of N$^ε$-trifluoroacetyl L-lysine (1.01 g, 3.73 mM), are placed in a single-neck flask (100 mL) with a magnetic stirrer. To this mixture is added 40 mL of dioxane. Diethylamine (10 µL) is added. The resulting mixture is stirred for 48 hours at a temperature of approximately 25° C. The mixture is slowly poured into 100 mL water while stirring. A solid is precipitated. The solid is filtered and washed with water. The solid is resuspended in 100 mL water and filtered. The solid is kept under vacuum for approximately 12 hours.

Example 28

Cleavage of γ-Benzyl Moiety from the Polypeptide Prepared in Example 27

The protected polypeptide prepared in Example 27, 100 mg, is suspended in tetrahydrofuran (20 mL) and cooled in an ice water bath. Concentrated sulfuric acid, 4 mL, is added. The resulting clear solution is stirred for 20 hours at a temperature of approximately 25° C. The solvent, tetrahydrofuran, is removed by evaporation at 25° C. to form a viscous liquid. Water, 50 mL, is added to the viscous liquid with stirring. A white precipitate forms which is filtered under vacuum and dried over phosphorous pentoxide under vacuum at 25° C. for approximately 12 hours in the dark. A white solid is obtained. The solid is filtered and dried in a dessicator under vacuum. The yield is determined to be 75 mg.

Example 29

Cleavage of γ-Benzyl Moiety from the Polypeptide Prepared in Example 27

The protected polypeptide prepared in Example 27, 1 g, is suspended in 50 mL of a mixture prepared of 47 mL concentrated HCl adjusted to 100 mL with glacial acetic acid. The starting material slowly dissolves forming a slightly turbid solution. The mixture is stirred for 18 hours at a temperature of approximately 22° C. The solution is poured into 1,000 mL of stirred water. A white precipitate is formed. The suspension is stirred for another 3 hours and then filtered. The product is washed with water and dried under vacuum at 50° C. for approximately 17 hours.

Example 30

Evaluation of Amines to be Used to Cleave the N$^ε$-Trifluoroacetyl Moiety from the Polypeptide Prepared in Example 28

The polypeptide prepared in Example 28, 75 mg, is suspended in 15 mL of water. An amine, 7 mL, is added to the suspension to provide an amine concentration of 3 M. A list of amines is provided in Table IV. Since a deprotected polypeptide is soluble in water, the reaction is monitored by the clarity of the solution. The results for each of the amines are summarized in Table IV.

TABLE IV

| Amine | Result |
| --- | --- |
| Morpholine | No clear solution after 48 hours. |
| N-methyl-piperazine | No clear solution after 48 hours. |
| Dicyclohexylamine | No clear solution after 48 hours. |

TABLE IV-continued

| Amine | Result |
| --- | --- |
| Di-sec-butylamine | No clear solution after 48 hours. |
| Pyrrolidine | No clear solution after 48 hours. |
| Diisopropylamine | Clear solution after about 1 hour. |
| Dipropylamine | No clear solution after 48 hours. |
| Isopropylamine | Clear solution after about 1.5 hours. |
| Methylamine (aqueous) | No clear solution after 48 hours. |

The results in Table IV clearly show that a free base form of the polypeptide prepared in Example 28 is formed only upon the addition of diisopropylamine or isopropylamine. The results in Table I also show that dipropylamine, morpholine, N-methyl-piperazine, dicyclohexylamine, di-sec-butylamine, pyrrolidine, and methylamine failed to produce a free base form of the polypeptide.

Thus, applicants unexpectedly determined that in the second deprotection step of the process of the invention, Step (b), diisopropylamine and isopropylamine were the only amines that successfully removed the $N^\epsilon$-trifluoroacetyl group of the lysine moiety.

Example 31

Cleavage of the $N^\epsilon$-Trifluoroacetyl Moiety from the Polypeptide Prepared in Example 28

The polypeptide prepared in Example 28, 75 mg, is suspended in 15 mL of water. Diisopropylamine, 7 mL, is added to the suspension to provide an amine concentration of 3M. A milky-white solution becomes clear in approximately 1 hour and the clear solution is stirred at 25° C. for 20 hours. The reaction mixture is evaporated at approximately 25° C. to form crude glatiramer free base in the form of a viscous liquid. Fifty percent (50%) acetic acid (15 mL) is added to the mixture and stirred for 30 minutes to form a glatiramer acetate solution.

Example 32

Diafiltration

Tangential Flow Filtration

The glatiramer acetate solution prepared in Example 31 is diluted to 120 mL with water. The dilute solution is first filtered through a 30 K diafiltration membrane, Pellicon XL, PLCCC 10 (50 cm$^2$), available from Millipore, and then, filtered through a 3 K diafiltration membrane, Pellicon XL, PLCCC 5 (50 cm$^2$), available from Millipore. The concentrated solution obtained is lyophilized to provide glatiramer acetate in solid form.

Example 33

Chromatographic Method of Purification of Glatiramer Acetate

The glatiramer acetate solution prepared in Example 31 is concentrated in vacuo to dryness and subjected to chromatographic separation. A column for gel filtration, FRACTOGEL TSK HW55 (600×26 mm) is prepared in a Superformance 26 Merck cartridge according to the manufacturer's instructions. The column is equilibrated with 0.2 M ammonium acetate buffer pH 5.0, 30 mL of glatiramer free base solution samples (20 mg/mL, in 0.2 M ammonium acetate pH 5.0) are loaded on the column and fractions are collected. A fraction having an average molecular weight of 7-10 kDa is isolated.

While the invention has been described with particular reference to certain embodiments thereof, it will be understood that changes and modifications may be made by those of ordinary skill within the scope and spirit of the following claims:

What is claimed is:

1. A process for preparing a glatiramer polypeptide comprising L-tyrosine, L-alanine, L-glutamate and L-lysine, or a pharmaceutically acceptable salt thereof, wherein said process comprises:
    (i) polymerizing a mixture of N-carboxyanhydride of L-tyrosine, N-carboxyanhydride of L-alanine, N-carboxyanhydride of protected L-glutamate and N-carboxyanhydride of N-t-butoxycarbonyl L-lysine, in a polar aprotic solvent in the presence of an alkylamine initiator, to form a protected glatiramer polypeptide, wherein the protected L-glutamate is selected from the group consisting of γ-p-methoxybenzyl L-glutamate, γ-benzyl L-glutamate and mixtures thereof; and
    (ii) adding an acid to the protected glatiramer polypeptide formed in Step (i) to form a glatiramer polypeptide or a pharmaceutically acceptable salt thereof, wherein said acid cleaves the γ-p-methoxybenzyl group from the glutamate moiety and the N-t-butoxycarbonyl group from the lysine moiety;
    wherein the acid is selected from the group consisting of trifluoroacetic acid, a mixture of acetic acid and hydrochloric acid, a mixture of acetic acid and sulfuric acid, and combinations thereof.

2. A process for preparing glatiramer acetate comprising:
    (a) polymerizing a mixture of N-carboxyanhydride of L-tyrosine, N-carboxyanhydride of L-alanine, N-carboxyanhydride of protected L-glutamate and N-carboxyanhydride of N-t-butoxycarbonyl L-lysine, in a polar aprotic solvent in the presence of an alkylamine initiator, to form a protected glatiramer, wherein the protected L-glutamate is selected from the group consisting of γ-p-methoxybenzyl L-glutamate, γ-benzyl L-glutamate, and mixtures thereof;
    (b) adding an acid to the protected glatiramer formed in Step (a) to form a glatiramer, wherein said acid cleaves the γ-p-methoxybenzyl group from the glutamate moiety and the N-t-butoxycarbonyl group from the lysine moiety, and wherein said acid is selected from the group consisting of trifluoroacetic acid, a mixture of acetic acid and hydrochloric acid, a mixture of acetic acid and sulfuric acid, and combinations thereof; and
    (c) treating the glatiramer formed in Step (b) with acetic acid to form glatiramer acetate.

3. The process according to claim 1, wherein the acid is a mixture of acetic acid and hydrochloric acid.

4. The process according to claim 1, wherein the acid is a mixture of acetic acid and sulfuric acid.

5. The process according to claim 1, wherein the acid is trifluoroacetic acid.

6. The process according to claim 2, wherein the glatiramer acetate has a weight average molecular weight of about 2 kDa to about 30 kDa.

7. The process according to claim 6, wherein the glatiramer acetate has a weight average molecular weight of about 4.7 kDa to about 11 kDa.

8. The process according to claim 7, wherein the glatiramer acetate has a weight average molecular weight of about 7 kDa to about 10 kDa.

9. The process according to claim 1, wherein the glatiramer polypeptide is substantially free of polypeptide fragments having a molecular weight of greater than about 40 kDa.

10. The process according to claim 1, wherein the glatiramer polypeptide is substantially free of polypeptide fragments having a molecular weight of less than about 2 kDa.

11. The process according to claim 1, wherein Step (ii) is conducted at a temperature of from about 10° C. to about 40° C.

12. The process according to claim 11, wherein Step (ii), is conducted at a temperature of from about 15° C. to about 30° C.

13. The process according to claim 12, wherein Step (ii), is conducted at a temperature of about 22° C. to about 25° C.

14. The process according to claim 1, wherein the initiator is diethylamine.

15. The process according to claim 1, wherein the polar aprotic solvent is selected from the group consisting of tetrahydrofuran, ethyl acetate, dimethyl furan, dimethylformamide, 1,4-dioxane, dimethoxyethane, 1,2-dichloroethylene, dimethylsulfoxide, dichloromethane and mixtures thereof.

16. The process according to claim 15, wherein the polar aprotic solvent is 1,4-dioxane.

17. The process according to claim 15, wherein the polar aprotic solvent is tetrahydrofuran.

18. The process according to claim 1, wherein the acid is present in an amount of from about 0.1 weight percent (wt. %) to about 100 wt. %, based on the total weight of the glatiramer polypeptide or pharmaceutically acceptable salt thereof.

19. The process according to claim 18, wherein the acid is present in an amount of from about 1 wt. % to about 10 wt. %, based on the total weight of the glatiramer polypeptide or pharmaceutically acceptable salt thereof.

20. The process according to claim 19, wherein the acid is present in an amount of from about 2 wt. % to about 6 wt. %, based on the total weight of the glatiramer polypeptide or pharmaceutically acceptable salt thereof.

* * * * *